(12) United States Patent
Fritz

(10) Patent No.: US 10,751,220 B2
(45) Date of Patent: Aug. 25, 2020

(54) METHOD OF FORMING BONDS BETWEEN DISCRETE COMPONENTS OF DISPOSABLE ARTICLES

(71) Applicant: Curt G. Joa, Inc., Sheboygan Falls, WI (US)

(72) Inventor: Jeff W. Fritz, Plymouth, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 0 days.

(21) Appl. No.: 13/771,402

(22) Filed: Feb. 20, 2013

(65) Prior Publication Data

US 2013/0213566 A1    Aug. 22, 2013

Related U.S. Application Data

(60) Provisional application No. 61/600,877, filed on Feb. 20, 2012.

(51) Int. Cl.
*A61F 13/15* (2006.01)
*A61F 13/00* (2006.01)

(52) U.S. Cl.
CPC .. *A61F 13/00987* (2013.01); *A61F 13/15699* (2013.01); *A61F 13/15747* (2013.01); *Y10T 156/1051* (2015.01)

(58) Field of Classification Search
CPC ................................................ A61F 13/15756
USPC ............................................................ 156/227
See application file for complete search history.

(56) References Cited

U.S. PATENT DOCUMENTS

| 135,145 A | 1/1873 | Murphy |
| 293,353 A | 2/1884 | Purvis |
| 312,257 A | 2/1885 | Cotton et al. |
| 410,123 A | 8/1889 | Stilwell |
| 432,742 A | 7/1890 | Stanley |
| 643,821 A | 2/1900 | Howlett |
| 1,393,524 A | 10/1921 | Grupe |
| 1,431,315 A | 10/1922 | Le Moine |
| 1,605,842 A | 11/1926 | Jones |
| 1,686,595 A | 10/1928 | Belluche |
| 1,957,651 A | 5/1934 | Joa |
| 2,009,857 A | 7/1935 | Potdevin |
| 2,054,832 A | 9/1936 | Potdevin |
| 2,117,432 A | 5/1938 | Linscott |
| 2,128,746 A | 8/1938 | Joa |

(Continued)

FOREIGN PATENT DOCUMENTS

| BE | 1007854 | 11/1995 |
| CA | 1146129 | 5/1983 |

(Continued)

OTHER PUBLICATIONS

International Search Report dated Jun. 3, 2013 regarding EP Application No. 13156051.8. 4 pages.

*Primary Examiner* — Barbara J Musser
(74) *Attorney, Agent, or Firm* — Ziolkowski Patent Solutions Group, SC

(57) ABSTRACT

Continuous edge folds of a top sheet in disposable products prepare the top sheet for placement/attachment of discrete side panels to the folded-over portion of top-sheets oriented so that the side panels lay on top of the top-sheet without any further folding steps required. Later, a back sheet can be added and back sheet edges then folded over to cover edges of top-sheet/side panel sandwich.

17 Claims, 3 Drawing Sheets

(56) References Cited

U.S. PATENT DOCUMENTS

| | | |
|---|---|---|
| 2,131,808 A | 10/1938 | Joa |
| 2,164,408 A | 7/1939 | Joa |
| 2,167,179 A | 7/1939 | Joa |
| 2,171,741 A | 9/1939 | Cohn et al. |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,627,859 A | 2/1953 | Hargrave |
| 2,695,025 A | 11/1954 | Andrews |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,788,786 A | 4/1957 | Dexter |
| 2,811,905 A | 11/1957 | Kennedy, Jr. |
| 2,828,745 A | 4/1958 | Deutz |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,890,700 A | 6/1959 | Lonberg-Holm |
| 2,913,862 A | 11/1959 | Sabee |
| 2,939,461 A | 6/1960 | Joa |
| 2,939,646 A | 6/1960 | Stone |
| 2,960,143 A | 11/1960 | Joa |
| 2,990,081 A | 6/1961 | De Neui et al. |
| 2,991,739 A | 7/1961 | Joa |
| 3,016,207 A | 1/1962 | Comstock, III |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,075,684 A | 1/1963 | Rothmann |
| 3,086,253 A | 4/1963 | Joa |
| 3,087,689 A | 4/1963 | Heim |
| 3,089,494 A | 5/1963 | Schwartz |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,318,608 A | 5/1967 | Smrekar |
| 3,322,589 A | 5/1967 | Joa |
| 3,336,847 A | 8/1967 | Johnson |
| 3,342,184 A | 9/1967 | Joa |
| 3,356,092 A | 12/1967 | Joa |
| 3,360,103 A | 12/1967 | Joa |
| 3,391,777 A | 7/1968 | Joa |
| 3,454,442 A | 7/1969 | Heller, Jr. |
| 3,463,413 A | 8/1969 | Smith |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,527,123 A | 9/1970 | Dovey |
| 3,538,551 A | 11/1970 | Joa |
| 3,540,641 A | 11/1970 | Besnyo |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger et al. |
| 3,728,191 A | 4/1973 | Wierzba et al. |
| 3,745,947 A | 7/1973 | Brocklehurst |
| 3,751,224 A | 8/1973 | Wackerle |
| 3,758,102 A | 9/1973 | Munn et al. |
| 3,762,542 A | 10/1973 | Grimes |
| 3,772,120 A | 11/1973 | Radzins |
| 3,776,798 A | 12/1973 | Milano |
| 3,796,360 A | 3/1974 | Alexeff |
| 3,811,987 A | 5/1974 | Wilkinson et al. |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,901,238 A | 8/1975 | Geller et al. |
| 3,903,768 A | 9/1975 | Amberg et al. |
| 3,904,147 A | 9/1975 | Taitel et al. |
| 3,918,968 A | 11/1975 | Coast |
| 3,921,481 A | 11/1975 | Fleetwod |
| 3,941,038 A | 3/1976 | Bishop |
| 3,960,646 A | 6/1976 | Wiedamann |
| 3,988,194 A | 10/1976 | Babcock et al. |
| 3,991,994 A | 11/1976 | Farish |
| 4,002,005 A | 1/1977 | Mueller et al. |
| 4,003,298 A | 1/1977 | Schott, Jr. |
| 4,009,626 A | 3/1977 | Gressman |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,220,237 A | 9/1980 | Mohn |
| 4,222,533 A | 9/1980 | Pongracz |
| 4,223,822 A | 9/1980 | Clitheroe |
| 4,231,129 A | 11/1980 | Winch |
| 4,234,157 A | 11/1980 | Hodgeman et al. |
| 4,236,955 A | 12/1980 | Prittie |
| 4,275,510 A | 6/1981 | George |
| 4,284,454 A | 8/1981 | Joa |
| 4,297,157 A | 10/1981 | Van Vilet |
| 4,307,800 A | 12/1981 | Joa |
| 4,316,756 A | 2/1982 | Wilson |
| 4,325,519 A | 4/1982 | McLean |
| 4,342,206 A | 8/1982 | Rommel |
| 4,349,140 A | 9/1982 | Passafiume |
| 4,364,787 A | 12/1982 | Radzins |
| 4,374,576 A | 2/1983 | Ryan |

(56) References Cited

U.S. PATENT DOCUMENTS

| | | |
|---|---|---|
| 4,379,008 A | 4/1983 | Gross et al. |
| 4,394,898 A | 7/1983 | Campbell |
| 4,411,721 A | 10/1983 | Wishart |
| 4,426,897 A | 1/1984 | Littleton |
| 4,452,597 A | 6/1984 | Achelpohl |
| 4,479,836 A | 10/1984 | Dickover et al. |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,543,152 A | 9/1985 | Nozaka |
| 4,551,191 A | 11/1985 | Kock et al. |
| 4,578,133 A | 3/1986 | Oshefsky et al. |
| 4,586,199 A | 5/1986 | Birring |
| 4,589,945 A | 5/1986 | Polit |
| 4,603,800 A | 8/1986 | Focke et al. |
| 4,606,964 A | 8/1986 | Wideman |
| 4,608,115 A | 8/1986 | Schroth et al. |
| 4,610,681 A | 9/1986 | Strohbeen et al. |
| 4,610,682 A | 9/1986 | Kopp |
| 4,614,076 A | 9/1986 | Rathemacher |
| 4,619,357 A | 10/1986 | Radzins et al. |
| 4,625,612 A | 12/1986 | Oliver |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,173 A | 3/1987 | Johnson et al. |
| 4,650,530 A | 3/1987 | Mahoney et al. |
| 4,663,220 A | 5/1987 | Wisneski et al. |
| 4,672,705 A | 6/1987 | Bors et al. |
| 4,675,016 A | 6/1987 | Meuli et al. |
| 4,675,062 A | 6/1987 | Instance |
| 4,675,068 A | 6/1987 | Lundmark |
| 4,686,136 A | 8/1987 | Homonoff et al. |
| 4,693,056 A | 9/1987 | Raszewski |
| 4,701,239 A | 10/1987 | Craig |
| 4,720,415 A | 1/1988 | Vander Wielen et al. |
| 4,723,698 A | 2/1988 | Schoonderbeek |
| 4,726,874 A | 2/1988 | Van Vliet |
| 4,726,876 A | 2/1988 | Tomsovic, Jr. |
| 4,743,241 A | 5/1988 | Igaue et al. |
| 4,751,997 A | 6/1988 | Hirsch |
| 4,753,429 A | 6/1988 | Irvine et al. |
| 4,756,141 A | 7/1988 | Hirsch et al. |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,782,647 A | 11/1988 | Williams et al. |
| 4,785,986 A | 11/1988 | Daane et al. |
| 4,795,451 A | 1/1989 | Buckley |
| 4,795,510 A | 1/1989 | Wittrock et al. |
| 4,798,353 A | 1/1989 | Peugh |
| 4,801,345 A | 1/1989 | Dussaud et al. |
| 4,802,570 A | 2/1989 | Hirsch et al. |
| 4,826,499 A | 5/1989 | Ahr |
| 4,840,609 A | 6/1989 | Jones et al. |
| 4,845,964 A | 7/1989 | Bors et al. |
| 4,864,802 A | 9/1989 | D'Angelo |
| 4,880,102 A | 11/1989 | Indrebo |
| 4,888,231 A | 12/1989 | Angstadt |
| 4,892,536 A | 1/1990 | Des Marais et al. |
| 4,904,440 A | 2/1990 | Angstadt |
| 4,908,175 A | 3/1990 | Angstadt |
| 4,909,019 A | 3/1990 | Delacretaz et al. |
| 4,915,767 A | 4/1990 | Rajala et al. |
| 4,917,746 A | 4/1990 | Kons |
| 4,925,520 A | 5/1990 | Beaudoin et al. |
| 4,927,322 A | 5/1990 | Schweizer et al. |
| 4,927,486 A | 5/1990 | Fattal et al. |
| 4,927,582 A | 5/1990 | Bryson |
| 4,937,887 A | 7/1990 | Schreiner |
| 4,963,072 A | 10/1990 | Miley et al. |
| 4,987,940 A | 1/1991 | Straub et al. |
| 4,994,010 A | 2/1991 | Doderer-Winkler |
| 5,000,806 A | 3/1991 | Merkatoris et al. |
| 5,021,111 A | 6/1991 | Swenson |
| 5,025,910 A | 6/1991 | Lasure et al. |
| 5,029,505 A | 7/1991 | Holliday |
| 5,045,039 A | 9/1991 | Bay |
| 5,045,135 A | 9/1991 | Meissner et al. |
| 5,062,597 A | 11/1991 | Martin et al. |
| 5,064,179 A | 11/1991 | Martin |
| 5,064,492 A | 11/1991 | Friesch |
| 5,080,741 A | 1/1992 | Nomura et al. |
| 5,094,658 A | 3/1992 | Smithe et al. |
| 5,096,532 A | 3/1992 | Neuwirth et al. |
| 5,108,017 A | 4/1992 | Adamski, Jr. et al. |
| 5,109,767 A | 5/1992 | Nyfeler et al. |
| 5,110,403 A | 5/1992 | Ehlert |
| 5,127,981 A | 7/1992 | Straub et al. |
| 5,131,525 A | 7/1992 | Musschoot |
| 5,131,901 A | 7/1992 | Moll |
| 5,133,511 A | 7/1992 | Mack |
| 5,147,487 A | 9/1992 | Nomura et al. |
| 5,163,594 A | 11/1992 | Meyer |
| 5,171,239 A | 12/1992 | Igaue et al. |
| 5,176,244 A | 1/1993 | Radzins et al. |
| 5,183,252 A | 2/1993 | Wolber et al. |
| 5,188,627 A | 2/1993 | Igaue et al. |
| 5,190,234 A | 3/1993 | Ezekiel |
| 5,195,684 A | 3/1993 | Radzins |
| 5,203,043 A | 4/1993 | Riedel |
| 5,213,645 A | 5/1993 | Nomura et al. |
| 5,222,422 A | 6/1993 | Benner, Jr. et al. |
| 5,223,069 A | 6/1993 | Tokuno et al. |
| 5,226,992 A | 7/1993 | Morman |
| 5,246,433 A | 9/1993 | Hasse et al. |
| 5,252,228 A | 10/1993 | Stokes |
| 5,267,933 A | 12/1993 | Precoma |
| 5,273,228 A | 12/1993 | Yoshida |
| 5,275,076 A | 1/1994 | Greenwalt |
| 5,275,676 A | 1/1994 | Rooyakkers et al. |
| 5,308,345 A | 5/1994 | Herrin |
| 5,328,438 A | 7/1994 | Crowley |
| 5,334,446 A | 8/1994 | Quantrille et al. |
| 5,340,424 A | 8/1994 | Matsushita |
| 5,353,909 A | 10/1994 | Mukai |
| 5,368,893 A | 11/1994 | Sommer et al. |
| 5,389,173 A | 2/1995 | Merkatoris et al. |
| 5,393,360 A | 2/1995 | Bridges et al. |
| 5,407,507 A | 4/1995 | Ball |
| 5,407,513 A | 4/1995 | Hayden et al. |
| 5,410,857 A | 5/1995 | Utley |
| 5,415,649 A | 5/1995 | Watanabe et al. |
| 5,417,132 A | 5/1995 | Cox et al. |
| 5,421,924 A | 6/1995 | Ziegelhoffer et al. |
| 5,424,025 A | 6/1995 | Hanschen et al. |
| 5,429,576 A | 7/1995 | Doderer-Winkler |
| 5,435,802 A | 7/1995 | Kober |
| 5,435,971 A | 7/1995 | Dyckman |
| 5,449,353 A | 9/1995 | Watanabe et al. |
| 5,464,401 A | 11/1995 | Hasse et al. |
| 5,486,253 A | 1/1996 | Otruba |
| 5,494,622 A | 2/1996 | Heath et al. |
| 5,500,075 A | 3/1996 | Herrmann |
| 5,516,392 A | 5/1996 | Bridges et al. |
| 5,518,566 A | 5/1996 | Bridges et al. |
| 5,525,175 A | 6/1996 | Blenke et al. |
| 5,531,850 A | 7/1996 | Herrmann |
| 5,540,647 A | 7/1996 | Weiermann et al. |
| 5,540,796 A | 7/1996 | Fries |
| 5,545,275 A | 8/1996 | Herrin et al. |
| 5,545,285 A | 8/1996 | Johnson |
| 5,552,013 A | 9/1996 | Ehlert et al. |
| 5,555,786 A | 9/1996 | Fuller |
| 5,556,360 A | 9/1996 | Kober et al. |
| 5,556,504 A | 9/1996 | Rajala et al. |
| 5,560,793 A | 10/1996 | Ruscher et al. |
| 5,575,187 A | 11/1996 | Dieterlen |
| 5,586,964 A | 12/1996 | Chase |
| 5,602,747 A | 2/1997 | Rajala |
| 5,603,794 A | 2/1997 | Thomas |

(56) References Cited

U.S. PATENT DOCUMENTS

| | | |
|---|---|---|
| 5,624,420 A | 4/1997 | Bridges et al. |
| 5,624,428 A | 4/1997 | Sauer |
| 5,628,738 A | 5/1997 | Suekane |
| 5,634,917 A | 6/1997 | Fujioka et al. |
| 5,636,500 A | 6/1997 | Gould |
| 5,643,165 A | 7/1997 | Klekamp |
| 5,643,396 A | 7/1997 | Rajala et al. |
| 5,645,543 A | 7/1997 | Nomura et al. |
| 5,659,229 A | 8/1997 | Rajala |
| 5,660,657 A | 8/1997 | Rajala et al. |
| 5,660,665 A | 8/1997 | Jalonen |
| 5,683,376 A | 11/1997 | Kato et al. |
| 5,683,531 A | 11/1997 | Roessler et al. |
| 5,685,873 A | 11/1997 | Bruemmer |
| RE35,687 E | 12/1997 | Igaue et al. |
| 5,693,165 A | 12/1997 | Schmitz |
| 5,699,653 A | 12/1997 | Hartman et al. |
| 5,705,013 A | 1/1998 | Nease |
| 5,707,470 A | 1/1998 | Rajala et al. |
| 5,711,832 A | 1/1998 | Glaug et al. |
| 5,725,518 A | 3/1998 | Coates |
| 5,725,714 A | 3/1998 | Fujioka |
| 5,743,994 A | 4/1998 | Roessler et al. |
| 5,745,922 A | 5/1998 | Rajala et al. |
| 5,746,869 A | 5/1998 | Hayden et al. |
| 5,749,989 A | 5/1998 | Linman et al. |
| 5,759,340 A | 6/1998 | Boothe et al. |
| 5,766,389 A | 6/1998 | Brandon et al. |
| 5,766,411 A | 6/1998 | Wilson |
| 5,779,689 A | 7/1998 | Pfeifer et al. |
| 5,788,797 A | 8/1998 | Herrin et al. |
| 5,817,199 A | 10/1998 | Brennecke et al. |
| 5,827,259 A | 10/1998 | Laux et al. |
| 5,829,164 A | 11/1998 | Kotischke |
| 5,836,931 A | 11/1998 | Toyoda et al. |
| 5,858,012 A | 1/1999 | Yamaki et al. |
| 5,865,393 A | 2/1999 | Kreft et al. |
| 5,868,727 A | 2/1999 | Barr et al. |
| 5,876,027 A | 3/1999 | Fukui et al. |
| 5,876,792 A | 3/1999 | Caldwell |
| 5,879,500 A | 3/1999 | Herrin et al. |
| 5,902,431 A | 5/1999 | Wilkinson et al. |
| 5,904,675 A | 5/1999 | Laux et al. |
| 5,932,039 A | 8/1999 | Popp et al. |
| 5,935,367 A | 8/1999 | Hollenbeck |
| 5,938,193 A | 8/1999 | Bluemle et al. |
| 5,938,652 A | 8/1999 | Sauer |
| 5,964,390 A | 10/1999 | Borresen et al. |
| 5,964,970 A | 10/1999 | Woolwine et al. |
| 5,971,134 A | 10/1999 | Trefz et al. |
| 5,983,764 A | 11/1999 | Hillebrand |
| 6,009,781 A | 1/2000 | McNeil |
| 6,022,443 A | 2/2000 | Rajala et al. |
| 6,036,805 A | 3/2000 | McNichols |
| 6,043,836 A | 3/2000 | Kerr et al. |
| 6,050,517 A | 4/2000 | Dobrescu et al. |
| 6,074,110 A | 6/2000 | Verlinden et al. |
| 6,076,442 A | 6/2000 | Arterburn et al. |
| 6,080,909 A | 6/2000 | Osterdahl et al. |
| 6,098,249 A | 8/2000 | Toney et al. |
| 6,123,792 A | 9/2000 | Samida et al. |
| 6,142,048 A | 11/2000 | Bradatsch et al. |
| 6,171,432 B1 | 1/2001 | Brisebois |
| 6,183,576 B1 | 2/2001 | Couillard et al. |
| 6,193,054 B1 | 2/2001 | Henson et al. |
| 6,193,702 B1 | 2/2001 | Spencer |
| 6,195,850 B1 | 3/2001 | Melbye |
| 6,210,386 B1 | 4/2001 | Inoue |
| 6,212,859 B1 | 4/2001 | Bielik, Jr. et al. |
| 6,214,147 B1 | 4/2001 | Mortellite et al. |
| 6,250,048 B1 | 6/2001 | Linkiewicz |
| 6,264,639 B1 | 7/2001 | Sauer |
| 6,264,784 B1 | 7/2001 | Menard et al. |
| 6,276,421 B1 | 8/2001 | Valenti et al. |
| 6,276,587 B1 | 8/2001 | Borresen |
| 6,280,373 B1 | 8/2001 | Lanvin |
| 6,284,081 B1 | 9/2001 | Vogt et al. |
| 6,287,409 B1 | 9/2001 | Stephany |
| 6,305,260 B1 | 10/2001 | Truttmann et al. |
| 6,306,122 B1 | 10/2001 | Narawa et al. |
| 6,309,336 B1 | 10/2001 | Muessig et al. |
| 6,312,420 B1 | 11/2001 | Sasaki et al. |
| 6,314,333 B1 | 11/2001 | Rajala et al. |
| 6,315,022 B1 | 11/2001 | Herrin et al. |
| 6,319,347 B1 | 11/2001 | Rajala |
| 6,336,921 B1 | 1/2002 | Kato et al. |
| 6,336,922 B1 | 1/2002 | VanGompel et al. |
| 6,336,923 B1 | 1/2002 | Fujioka et al. |
| 6,358,350 B1 | 3/2002 | Glaug et al. |
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturino et al. |
| 6,425,430 B1 | 7/2002 | Ward et al. |
| 6,431,038 B2 | 8/2002 | Couturier |
| 6,440,246 B1 | 8/2002 | Vogt et al. |
| 6,443,389 B1 | 9/2002 | Palone |
| 6,446,795 B1 | 9/2002 | Allen et al. |
| 6,473,669 B2 | 10/2002 | Rajala et al. |
| 6,475,325 B1 | 11/2002 | Parrish et al. |
| 6,478,786 B1 | 11/2002 | Glaug et al. |
| 6,482,278 B1 | 11/2002 | McCabe et al. |
| 6,494,244 B2 | 12/2002 | Parrish et al. |
| 6,514,233 B1 | 2/2003 | Glaug |
| 6,521,320 B2 | 2/2003 | McCabe et al. |
| 6,523,595 B1 | 2/2003 | Milner et al. |
| 6,524,423 B1 | 2/2003 | Hilt et al. |
| 6,533,879 B2 | 3/2003 | Quereshi et al. |
| 6,540,857 B1 | 4/2003 | Coenen et al. |
| 6,547,909 B1 | 4/2003 | Butterworth |
| 6,550,517 B1 | 4/2003 | Hilt et al. |
| 6,551,228 B1 | 4/2003 | Richards |
| 6,551,430 B1 | 4/2003 | Glaug et al. |
| 6,554,815 B1 | 4/2003 | Umebayashi |
| 6,569,275 B1 | 5/2003 | Popp et al. |
| 6,572,520 B2 | 6/2003 | Blumle |
| 6,581,517 B1 | 6/2003 | Becker et al. |
| 6,585,841 B1 | 7/2003 | Popp et al. |
| 6,589,149 B1 | 7/2003 | VanEperen et al. |
| 6,596,107 B2 | 7/2003 | Stopher |
| 6,596,108 B2 | 7/2003 | McCabe |
| 6,605,172 B1 | 8/2003 | Anderson et al. |
| 6,605,173 B2 | 8/2003 | Glaug et al. |
| 6,620,276 B1 | 9/2003 | Kuntze et al. |
| 6,632,209 B1 | 10/2003 | Chmielewski |
| 6,634,269 B2 | 10/2003 | Eckstein et al. |
| 6,637,583 B1 | 10/2003 | Anderson |
| 6,648,122 B1 | 11/2003 | Hirsch et al. |
| 6,649,010 B2 | 11/2003 | Parrish et al. |
| 6,656,309 B1 | 12/2003 | Parker et al. |
| 6,659,150 B1 | 12/2003 | Perkins et al. |
| 6,659,991 B2 | 12/2003 | Suekane |
| 6,675,552 B2 | 1/2004 | Kunz et al. |
| 6,682,626 B2 | 1/2004 | Mlinar et al. |
| 6,684,925 B2 | 2/2004 | Nagate et al. |
| 6,722,494 B2 | 4/2004 | Nakakado |
| 6,730,189 B1 | 5/2004 | Franzmann |
| 6,743,324 B2 | 6/2004 | Hargett et al. |
| 6,750,466 B2 | 6/2004 | Song |
| 6,758,109 B2 | 7/2004 | Nakakado |
| 6,766,817 B2 | 7/2004 | da Silva |
| 6,779,426 B2 | 8/2004 | Holliday |
| 6,808,582 B2 | 10/2004 | Popp et al. |
| D497,991 S | 11/2004 | Otsubo et al. |
| 6,811,019 B2 | 11/2004 | Christian et al. |
| 6,811,642 B2 | 11/2004 | Ochi |
| 6,814,217 B2 | 11/2004 | Blumenthal et al. |
| 6,820,671 B2 | 11/2004 | Calvert |
| 6,823,981 B2 | 11/2004 | Ogle et al. |
| 6,837,840 B2 | 1/2005 | Yonekawa et al. |
| 6,840,616 B2 | 1/2005 | Summers |
| 6,869,494 B2 | 3/2005 | Roessler et al. |
| 6,875,202 B2 | 4/2005 | Kumasaka et al. |
| 6,884,310 B2 | 4/2005 | Roessler et al. |

(56) References Cited

U.S. PATENT DOCUMENTS

| | | | |
|---|---|---|---|
| 6,893,528 B2 | 5/2005 | Middelstadt et al. |
| 6,913,718 B2 | 7/2005 | Ducker |
| 6,918,404 B2 | 7/2005 | Dias da Silva |
| 6,852,186 B1 | 12/2005 | Matsuda et al. |
| 6,976,521 B2 | 12/2005 | Mlinar |
| 6,978,486 B2 | 12/2005 | Zhou et al. |
| 7,017,321 B2 | 3/2006 | Salvoni |
| 7,017,820 B1 | 3/2006 | Brunner |
| 7,045,031 B2 | 5/2006 | Popp et al. |
| 7,047,852 B2 | 5/2006 | Franklin et al. |
| 7,048,725 B2 | 5/2006 | Kling et al. |
| 7,066,586 B2 | 6/2006 | da Silva |
| 7,069,970 B2 | 7/2006 | Tomsovic et al. |
| 7,077,393 B2 | 7/2006 | Ishida |
| 7,130,710 B2 | 10/2006 | Shechtman |
| 7,137,971 B2 | 11/2006 | Tanzer |
| 7,172,666 B2 | 2/2007 | Groves et al. |
| 7,175,584 B2 | 2/2007 | Maxton et al. |
| 7,195,684 B2 | 3/2007 | Satoh |
| 7,201,345 B2 | 4/2007 | Werner |
| 7,204,682 B2 | 4/2007 | Venturino et al. |
| 7,214,174 B2 | 5/2007 | Allen et al. |
| 7,214,287 B2 | 5/2007 | Shiomi |
| 7,220,335 B2 | 5/2007 | Van Gompel et al. |
| 7,247,219 B2 | 7/2007 | O'Dowd |
| 7,252,730 B2 | 8/2007 | Hoffman et al. |
| 7,264,686 B2 | 9/2007 | Thorson et al. |
| 7,303,708 B2 | 12/2007 | Andrews et al. |
| 7,326,311 B2 | 2/2008 | Krueger et al. |
| 7,332,459 B2 | 2/2008 | Collins et al. |
| 7,374,627 B2 | 5/2008 | McCabe |
| 7,380,213 B2 | 5/2008 | Pesin |
| 7,398,870 B2 | 7/2008 | McCabe |
| 7,399,266 B2 | 7/2008 | Aiolfi et al. |
| 7,449,084 B2 | 11/2008 | Nakakado |
| 7,452,436 B2 | 11/2008 | Andrews |
| 7,533,709 B2 | 5/2009 | Meyer |
| 7,537,215 B2 | 5/2009 | Beaudoin et al. |
| 7,587,966 B2 | 9/2009 | Nakakado et al. |
| 7,618,513 B2 | 11/2009 | Meyer |
| 7,638,014 B2 | 12/2009 | Coose et al. |
| 7,640,962 B2 | 1/2010 | Meyer et al. |
| 7,695,464 B2 | 4/2010 | Fletcher et al. |
| 7,703,599 B2 | 4/2010 | Meyer |
| 7,708,849 B2 | 5/2010 | McCabe |
| 7,770,712 B2 | 8/2010 | McCabe |
| 7,771,407 B2 | 8/2010 | Umebayashi |
| 7,780,052 B2 | 8/2010 | McCabe |
| 7,793,772 B2 | 9/2010 | Schafer |
| 7,811,403 B2 | 10/2010 | Andrews |
| 7,861,756 B2 | 1/2011 | Jenquin et al. |
| 7,871,400 B2 | 1/2011 | Sablone et al. |
| 7,909,956 B2 | 3/2011 | Coose et al. |
| 7,922,983 B2 | 4/2011 | Prokash et al. |
| 7,935,296 B2 | 5/2011 | Koele et al. |
| 7,975,584 B2 | 7/2011 | McCabe |
| 7,987,964 B2 | 8/2011 | McCabe |
| 8,007,484 B2 | 8/2011 | McCabe et al. |
| 8,007,623 B2 | 8/2011 | Andrews |
| 8,011,493 B2 | 9/2011 | Giuliani et al. |
| 8,016,972 B2 | 9/2011 | Andrews et al. |
| 8,025,652 B2 | 9/2011 | Hornung et al. |
| 8,062,279 B2 * | 11/2011 | Miyamoto ............... 604/385.27 |
| 8,062,459 B2 | 11/2011 | Nakakado et al. |
| 8,100,173 B2 | 1/2012 | Hornung et al. |
| 8,172,977 B2 | 5/2012 | Andrews et al. |
| 8,176,573 B2 | 5/2012 | Popp et al. |
| 8,178,035 B2 | 5/2012 | Edvardsson et al. |
| 8,182,624 B2 | 5/2012 | Handziak |
| 8,182,735 B2 | 5/2012 | Edvardsson |
| 8,182,736 B2 | 5/2012 | Edvardsson |
| 8,257,237 B2 | 9/2012 | Burns, Jr. et al. |
| 8,293,056 B2 | 10/2012 | McCabe |
| 8,381,489 B2 | 2/2013 | Freshwater et al. |
| 8,398,793 B2 | 3/2013 | Andrews et al. |
| 8,417,374 B2 | 4/2013 | Meyer et al. |
| 8,439,814 B2 | 5/2013 | Piantoni et al. |
| 8,460,495 B2 | 6/2013 | McCabe |
| 8,485,956 B2 | 7/2013 | Burns, Jr. et al. |
| 8,512,496 B2 | 8/2013 | Makimura |
| 8,656,817 B2 | 2/2014 | Fritz et al. |
| 8,663,411 B2 | 3/2014 | McCabe |
| 8,673,098 B2 | 3/2014 | McCabe |
| 2001/0012813 A1 | 8/2001 | Bluemle |
| 2001/0017181 A1 | 8/2001 | Otruba et al. |
| 2001/0035332 A1 | 11/2001 | Zeitler |
| 2001/0042591 A1 | 11/2001 | Milner et al. |
| 2002/0040630 A1 | 4/2002 | Piazza |
| 2002/0046802 A1 | 4/2002 | Tachibana et al. |
| 2002/0059013 A1 | 5/2002 | Rajala et al. |
| 2002/0096241 A1 | 7/2002 | Instance |
| 2002/0125105 A1 | 9/2002 | Nakakado |
| 2002/0162776 A1 | 11/2002 | Hergeth |
| 2002/0193776 A1 * | 12/2002 | Fernfors ............ A61F 13/15756 604/389 |
| 2003/0000620 A1 | 1/2003 | Herrin et al. |
| 2003/0015209 A1 | 1/2003 | Gingras et al. |
| 2003/0115660 A1 | 1/2003 | Hopkins |
| 2003/0051802 A1 | 3/2003 | Hargett et al. |
| 2003/0052148 A1 | 3/2003 | Rajala et al. |
| 2003/0066585 A1 | 4/2003 | McCabe |
| 2003/0083638 A1 | 5/2003 | Molee |
| 2003/0084984 A1 | 5/2003 | Glaug et al. |
| 2003/0089447 A1 | 5/2003 | Molee et al. |
| 2003/0121244 A1 | 7/2003 | Abba |
| 2003/0121614 A1 | 7/2003 | Tabor et al. |
| 2003/0135189 A1 | 7/2003 | Umebayashi |
| 2003/0150551 A1 | 8/2003 | Baker |
| 2004/0007328 A1 | 1/2004 | Popp et al. |
| 2004/0016500 A1 | 1/2004 | Tachibana et al. |
| 2004/0044325 A1 | 3/2004 | Corneliusson |
| 2004/0073187 A1 | 4/2004 | Karami |
| 2004/0084468 A1 | 5/2004 | Kelbert et al. |
| 2004/0087425 A1 | 5/2004 | Tony et al. |
| 2004/0098791 A1 | 5/2004 | Faulks |
| 2004/0112517 A1 | 6/2004 | Groves et al. |
| 2004/0157041 A1 | 8/2004 | Leboeuf et al. |
| 2004/0164482 A1 | 8/2004 | Edinger |
| 2004/0167493 A1 | 8/2004 | Jarpenberg et al. |
| 2004/0177737 A1 | 9/2004 | Adami |
| 2004/0182213 A1 | 9/2004 | Wagner et al. |
| 2004/0182497 A1 | 9/2004 | Lowrey |
| 2004/0216830 A1 | 11/2004 | Van Eperen |
| 2005/0000628 A1 | 1/2005 | Norrby |
| 2005/0022476 A1 | 2/2005 | Hamer et al. |
| 2005/0056678 A1 | 3/2005 | Nomura et al. |
| 2005/0077418 A1 | 4/2005 | Werner et al. |
| 2005/0101929 A1 | 5/2005 | Waksmundzki |
| 2005/0196538 A1 | 9/2005 | Sommer et al. |
| 2005/0230056 A1 | 10/2005 | Meyer et al. |
| 2005/0230449 A1 | 10/2005 | Meyer et al. |
| 2005/0233881 A1 | 10/2005 | Meyer |
| 2005/0234412 A1 | 10/2005 | Andrews et al. |
| 2005/0257881 A1 | 11/2005 | Coose et al. |
| 2005/0275148 A1 | 12/2005 | Beaudoin et al. |
| 2006/0011030 A1 | 1/2006 | Wagner et al. |
| 2006/0021300 A1 | 2/2006 | Tada et al. |
| 2006/0137298 A1 | 6/2006 | Oshita et al. |
| 2006/0201619 A1 | 9/2006 | Andrews |
| 2006/0224137 A1 | 10/2006 | McCabe et al. |
| 2006/0265867 A1 | 11/2006 | Schaap |
| 2006/0266465 A1 | 11/2006 | Meyer |
| 2007/0074953 A1 | 4/2007 | McCabe |
| 2007/0131343 A1 | 6/2007 | Nordang |
| 2007/0131817 A1 | 6/2007 | Fromm |
| 2008/0041206 A1 | 2/2008 | Mergola et al. |
| 2008/0125736 A1 | 5/2008 | Tsuji et al. |
| 2008/0208152 A1 * | 8/2008 | Eckstein et al. ............... 604/365 |
| 2008/0210067 A1 | 9/2008 | Schlinz et al. |
| 2008/0223537 A1 | 9/2008 | Wiedmann |
| 2008/0281286 A1 | 11/2008 | Peterson |
| 2008/0287898 A1 | 11/2008 | Guzman Reyes |
| 2009/0020211 A1 | 1/2009 | Andrews et al. |
| 2009/0126864 A1 | 5/2009 | Tachibana et al. |

(56) References Cited

U.S. PATENT DOCUMENTS

| | | | |
|---|---|---|---|
| 2009/0198205 A1 | 8/2009 | Malowaniec et al. | |
| 2009/0212468 A1 | 8/2009 | Edvardsson et al. | |
| 2010/0010465 A1* | 1/2010 | Winqvist | A61F 13/64 604/389 |
| 2010/0078119 A1 | 4/2010 | Yamamoto | |
| 2010/0078120 A1 | 4/2010 | Otsubo | |
| 2010/0078127 A1 | 4/2010 | Yamamoto | |
| 2010/0193135 A1 | 8/2010 | Eckstein et al. | |
| 2010/0193138 A1 | 8/2010 | Eckstein | |
| 2010/0193155 A1 | 8/2010 | Nakatani | |
| 2010/0249737 A1 | 9/2010 | Ito et al. | |
| 2011/0003673 A1 | 1/2011 | Piantoni et al. | |
| 2011/0106042 A1 | 5/2011 | Sablone et al. | |
| 2012/0079926 A1 | 4/2012 | Long et al. | |
| 2012/0123377 A1 | 5/2012 | Back | |
| 2012/0172828 A1* | 7/2012 | Koenig et al. | 604/385.201 |
| 2012/0270715 A1 | 10/2012 | Motegi et al. | |
| 2012/0285306 A1 | 11/2012 | Weibelt | |
| 2012/0310193 A1 | 12/2012 | Ostertag | |
| 2012/0312463 A1 | 12/2012 | Ogasawara et al. | |
| 2013/0066613 A1 | 3/2013 | Russell | |
| 2013/0079741 A1 | 3/2013 | Nakashita | |
| 2013/0239765 A1 | 9/2013 | McCabe et al. | |

FOREIGN PATENT DOCUMENTS

| | | |
|---|---|---|
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2330679 | 9/1999 |
| CA | 2404154 | 10/2001 |
| CA | 2541194 | 10/2006 |
| CA | 2559517 | 4/2007 |
| CA | 2337700 | 8/2008 |
| CA | 2407867 | 6/2010 |
| CA | 2699136 | 10/2010 |
| CA | 142627 | 6/2013 |
| CA | 2600432 | 7/2013 |
| CA | 2573445 | 3/2014 |
| CN | 202105105 | 1/2012 |
| DE | 60123502 | 10/2006 |
| DE | 60216550 | 12/2006 |
| DE | 102005035544 | 2/2007 |
| DE | 1020060472-80 | 4/2007 |
| DE | 102005048868 | 4/2007 |
| DE | 102007063209 | 6/2009 |
| EP | 0044206 | 1/1982 |
| EP | 0048011 | 3/1982 |
| EP | 0089106 | 9/1983 |
| EP | 0099732 | 2/1984 |
| EP | 0206208 | 12/1986 |
| EP | 0304140 | 2/1989 |
| EP | 0411287 | 2/1991 |
| EP | 0439897 | 8/1991 |
| EP | 0455231 A1 | 11/1991 |
| EP | 510251 | 10/1992 |
| EP | 0589859 | 3/1994 |
| EP | 0676352 | 4/1995 |
| EP | 0652175 A1 | 5/1995 |
| EP | 0811473 | 12/1997 |
| EP | 0901780 | 3/1999 |
| EP | 0990588 | 4/2000 |
| EP | 1132325 A2 | 9/2001 |
| EP | 1035818 | 4/2002 |
| EP | 1199057 | 4/2002 |
| EP | 1366734 | 12/2003 |
| EP | 1393701 | 3/2004 |
| EP | 1415628 | 5/2004 |
| EP | 1433731 | 6/2004 |
| EP | 1571249 | 9/2005 |
| EP | 1619008 | 1/2006 |
| EP | 1707168 A2 | 10/2006 |
| EP | 1726414 | 11/2006 |
| EP | 1302424 | 12/2006 |
| EP | 1801045 | 6/2007 |
| EP | 1870067 | 12/2007 |
| EP | 1941853 | 7/2008 |
| EP | 1961403 | 8/2008 |
| EP | 1994919 | 11/2008 |
| EP | 2180864 | 11/2008 |
| EP | 2211812 | 11/2008 |
| EP | 2103427 | 9/2009 |
| EP | 2233116 | 9/2010 |
| EP | 2238955 | 10/2010 |
| EP | 1175880 | 5/2012 |
| EP | 1868821 | 1/2013 |
| EP | 2036522 | 3/2013 |
| EP | 1272347 | 4/2013 |
| EP | 2032338 | 8/2013 |
| EP | 2332505 | 12/2013 |
| EP | 2412348 | 3/2014 |
| ES | 509706 | 11/1982 |
| ES | 520559 | 12/1983 |
| ES | 296211 | 12/1987 |
| ES | 200601373 | 7/2009 |
| ES | 2311349 | 9/2009 |
| FR | 2177355 | 11/1973 |
| FR | 2255961 | 7/1975 |
| FR | 1132325 | 10/2006 |
| FR | 2891811 | 4/2007 |
| GB | 191101501 A | 1/1912 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 1467470 | 3/1977 |
| GB | 2045298 | 10/1980 |
| GB | 2115775 | 9/1983 |
| GB | 2288316 | 10/1995 |
| IT | 1374910 | 5/2010 |
| IT | 1374911 | 5/2010 |
| JP | 428364 | 1/1992 |
| JP | 542180 | 2/1993 |
| JP | 576566 | 3/1993 |
| JP | 626160 | 2/1994 |
| JP | 626161 | 2/1994 |
| JP | 6197925 A | 7/1994 |
| JP | 9299398 | 11/1997 |
| JP | 10035621 | 2/1998 |
| JP | 10-277091 A | 10/1998 |
| JP | 2008-161300 | 7/2008 |
| SE | 0602047 | 5/2007 |
| SE | 0601003-7 | 6/2007 |
| SE | 0601145-6 | 10/2009 |
| WO | WO08155618 | 12/1988 |
| WO | WO93/15248 | 8/1993 |
| WO | WO9403301 | 2/1994 |
| WO | WO97/23398 | 7/1997 |
| WO | WO9732552 | 9/1997 |
| WO | WO9747265 | 12/1997 |
| WO | WO9747810 | 12/1997 |
| WO | WO9821134 | 5/1998 |
| WO | WO98/55298 | 12/1998 |
| WO | WO9907319 | 2/1999 |
| WO | WO9913813 A1 | 3/1999 |
| WO | WO9932385 | 7/1999 |
| WO | WO9965437 | 12/1999 |
| WO | WO0143682 | 6/2001 |
| WO | WO0172237 A2 | 10/2001 |
| WO | WO2003/031177 | 4/2003 |
| WO | WO04007329 | 1/2004 |
| WO | WO05075163 | 8/2005 |

(56) References Cited

FOREIGN PATENT DOCUMENTS

| | | |
|---|---|---|
| WO | WO2006038946 | 4/2006 |
| WO | WO07029115 | 3/2007 |
| WO | WO07039800 | 4/2007 |
| WO | WO2007126347 | 11/2007 |
| WO | WO08001209 | 1/2008 |
| WO | WO2008/015594 | 2/2008 |
| WO | WO2008037281 | 4/2008 |
| WO | WO2008/123348 | 10/2008 |
| WO | WO2009/065497 | 3/2009 |
| WO | WO2009/065500 | 3/2009 |
| WO | WO2010028786 | 3/2010 |
| WO | WO2011101773 | 8/2011 |
| WO | WO2012/123813 A1 | 9/2012 |
| WO | WO2014/021897 | 2/2014 |

\* cited by examiner

METHOD OF FORMING BONDS BETWEEN DISCRETE COMPONENTS OF DISPOSABLE ARTICLES

RELATED APPLICATION

This application claims the benefit of U.S. Provisional Patent Application Ser. No. 61/600,877, filed 20 Feb. 2012.

BACKGROUND OF THE INVENTION

In prior art methods, side panels are bonded to top sheets, and then the side panels are folded over for further processing, such as folding and packaging. In other methods, side panels are attached like fastening tape to top-sheets, then folded over for further processing.

Traditional methods may result in skewed side panel placement, wrinkled side panels, and skewed side panel folding.

SUMMARY OF THE INVENTION

A continuous edge fold of a top sheet prepares the top sheet for placement/attachment of discrete side panels to the folded-over portions of the top-sheet. The folded over portions are oriented so side panels can be applied and lay on top of top-sheet without any further folding steps required. Later, a back-sheet is added and back-sheet edges then can be folded over to cover edges of top-sheet/side panel sandwich.

By applying the cut panel to the pre-folded edge of the continuous top sheet web, it is easier to better control the squareness of the panel to the top sheet. This ultimately improves the quality and appearance of the ear fold in the finished product.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1A:
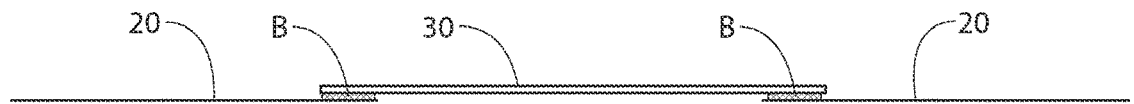
FIG. 1A is a cross sectional view of side panels bonded to a top sheet.
Figure 1B:
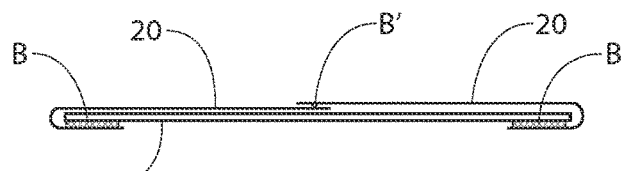
FIG. 1B is a cross sectional view of side panels bonded to a top sheet as in FIG. 1A, with the side panels folded over top sheet, with the side panels tack bonded (also known as fugitively bonded) to one another.

Referring now to FIG. 1A, a cross sectional view of side panels 20 bonded at bond sites B to a top sheet 30 is shown as constructed by prior art methods. As shown in FIG. 1B, side panels 20 are bonded to top sheet 30, and side panels 20 are folded over top sheet 30, with the side panels tack bonded (also known as fugitively bonded) to one another at bond site B'.

Figure 1C:
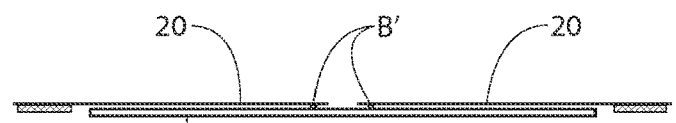
FIG. 1C is a cross sectional view of an alternative bonding pattern of the prior art, with a long portion of panel applied to a web and a short side folded over. This method was common for us and also had skewing issues.

Referring now to FIG. 1C a cross sectional view of an alternative bonding pattern of the prior art is shown, with a long portion of panel 20 is applied to a web 30 and a short side of the panel 20 (where the adhesive is shown) is then folded over (not shown, but similar in result to FIG. 1B).

These methods of the prior art presented skewing issues. Namely the side panels panels 20 could run somewhat off of parallel with the track of edges of top sheet 30.

Figure 2A:
FIG. 2A is a side view of a top sheet.
Figure 2B:
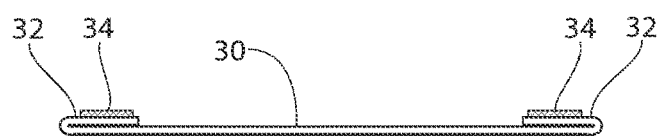
FIG. 2B is the top sheet of FIG. 2A, with continuous edges fold created along side edges of the top sheet, with adhesive applied to top regions of the continuous edge folds.
Figure 2C:
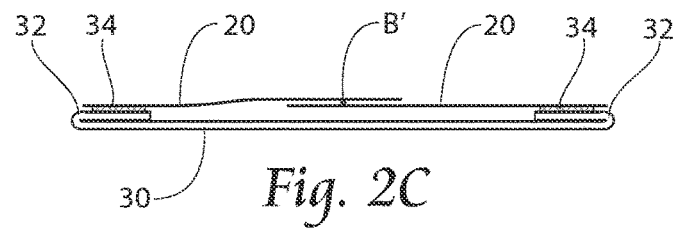
FIG. 2C is a side view of the top sheet of FIG. 2B, with side panels deposited atop the top sheet, and bonded to the top regions of the continuous edge folds, and the side panels tack bonded to one another.

Referring now to FIGS. 2A-2C, a first embodiment of the present invention is shown. Top sheet 30 is folded over at its edges to create continuous edge folds 32, and adhesive 34 is applied to top regions of the continuous edge folds 32 (and elsewhere in the drawings, where shown). Side panels 20 are deposited atop the top sheet 30, and bonded to the top regions of the continuous edge folds 32, and the side panels tack bonded to one another at bond site B'.

A method of forming bonds between discrete components of disposable articles is disclosed in FIGS. 2A-2C, the method comprising providing a top sheet layer 30 in a machine direction (the direction of view of the cross-sectional views of FIGS. 2A-2C), the top sheet layer having a first and a second cross-machine direction edge, generally at the left and the right of the views of FIGS. 2A-2C. Next a portion of the top sheet layer 30 is folded over at the two cross-machine direction edges (the left and the right edges layer 30 of FIGS. 2A-2C).

Adhesive 34 couples the side panels 20 to the top sheet 30. Preferably, the first and second side panels 20 overlap, and are bonded together with a fugitive, or temporary, or weak bond.

Figure 3:
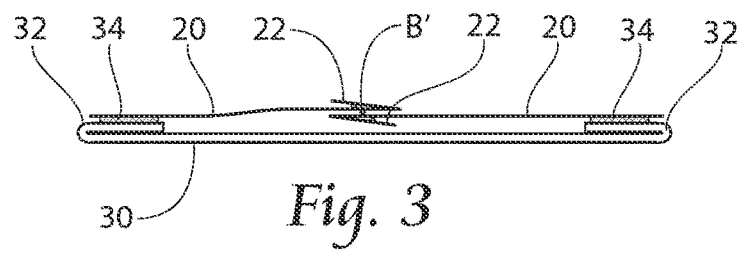
FIG. 3 is an alternative embodiment of the product shown in FIG. 2C, with the side panels provided with a pre-fold at the center-lying regions, which allows for longer length side panels.

Referring now to FIG. 3, an alternative embodiment of the product shown in FIG. 2C is shown, with the side panels 20 provided with pre-folds 22 at the center-lying regions of the side panels 20. This allows for longer length side panels.

Figure 4:
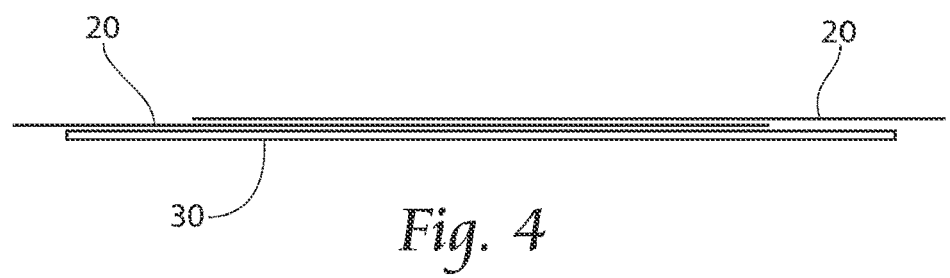
FIG. 4 is a side view of two side panels overlying a top sheet (preferably non-woven)
Figure 5:
FIG. 5 is a side view of two side panels overlying a top sheet (preferably non-woven) with continuous edge folds created along side edges of the top sheet.
Figure 6:
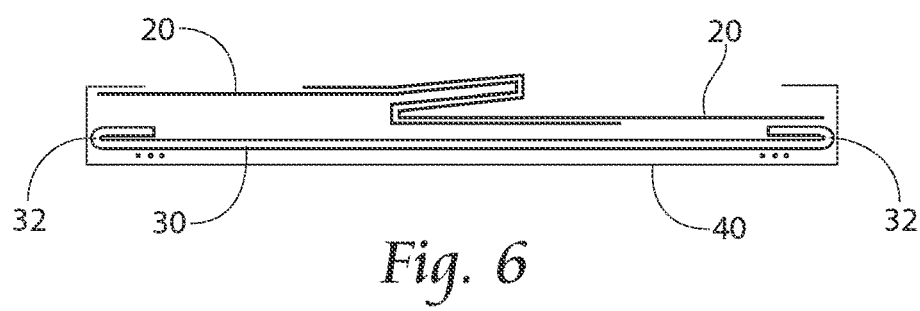
FIG. 6 is a side view of side panels which have been gathered, or pre-folded, for larger sized side panels, and coupled with continuous edge folds created along side edges of the top sheet, and a back sheet wrapped over the top sheet and side panels.
Figure 7:
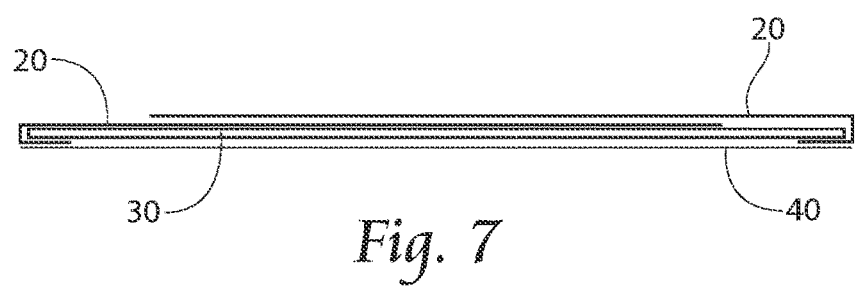
FIG. 7 is a finished product showing side panels which have been gathered, or pre-folded, for larger sized side panels, and coupled with continuous edge folds created along side edges of the top sheet, and a back sheet wrapped over the top sheet and side panels.
Figure 8:
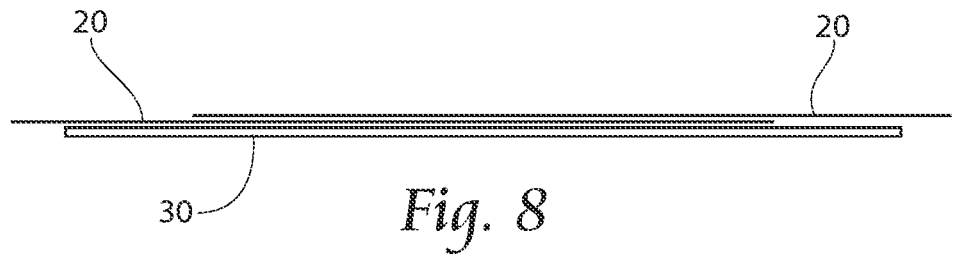
FIG. 8 is a side view of a top sheet overlain by side panels extending past edges of a top sheet.

Referring now to FIGS. 4-7, a second embodiment of the present invention is shown. FIG. 4 is a side view of two side panels 20 overlying a top sheet 30 (preferably non-woven), and as shown in FIG. 5 continuous edge folds 32 are created along side edges of the top sheet 30. As shown in FIG. 6, side panels 20 can be gathered, or pre-folded, for larger sized side panels 20, and coupled with continuous edge folds 32 created along side edges of the top sheet 30, and a back sheet 40 is wrapped over the top sheet 30 and side panels 20 as shown, to create a finished product as in FIG. 7, shown having laid back what previously were the top regions of the continuous edge folds 32, and having re-extended the previously pre-folded, for larger sized side panels 20.

Figure 9:
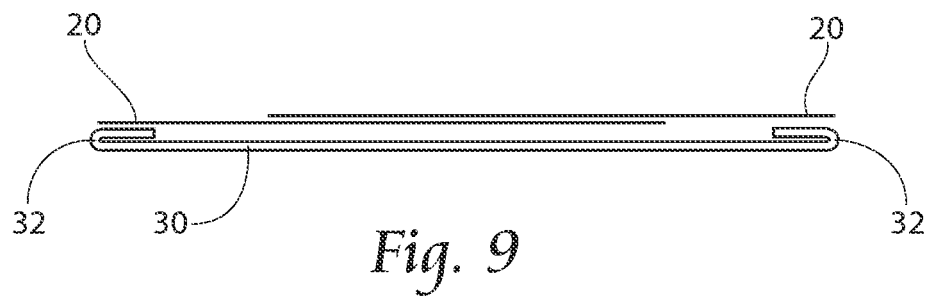
FIG. 9 is a side view of a top sheet overlain by side panels extending past edges of a top sheet, with continuous edge folds created along side edges of the top sheet.
Figure 10:
FIG. 10 is a side view of a top sheet overlain by side panels extending past edges of a top sheet, with continuous edge folds created along side edges of the top sheet, and a back sheet wrapped over the top sheet and side panels.
Figure 11:
FIG. 11 is a side view of finished product showing a top sheet overlain by side panels extending past edges of a top sheet, with continuous edge folds created along side edges of the top sheet, and a back sheet wrapped over the top sheet and side panels.

Referring now to FIGS. 8-11, a third embodiment of the present invention is shown. In this embodiment, top sheet 30 is overlain by side panels 20 extending past edges of top sheet 30, and continuous edge folds 32 are created along side edges of the top sheet 30 as shown in FIG. 9. A back sheet 40 is wrapped over the top sheet 30 and side panels 20 to create a finished product as shown in FIG. 11.

Steps of the method can comprise A1: Continuous top-sheet 30 is provided; A2. Fold edges of top-sheet 30 (folded portion to the top) to create folds 32; and A3. Intermittent adhesive is added to top of folded-over portion 32 of top-sheet 30. Alternatively, this adhesive could be applied to side panel 20 edges instead (which would then be step B1.5).

Next, step B1 can comprise Continuous side-panel 20 web provided (left and right, possible interfolded ends); and B2. Side panel 20 web cut to discrete parts (left and right, possible interfolded ends); and B3. Discrete side panel pieces 20 placed onto adhesive patches located on top-sheet folded edges 32.

Alternatively, step C1 can comprise a Back-sheet continuous web 40, and this can be added to any of the embodiments described above. A fugitive (or temporary) adhesive can be applied to keep side panel 20 ends temporarily attached to each other or to top-sheet 30 to control loose ends through downstream processing.

Still alternatively, top sheet 30 and an attached ear or side panel 20 can be composed as shown in FIGS. 2A-2C, and then unfolded prior to combining with back sheet 40.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A method of forming bonds between discrete components of disposable articles, the method comprising:
   providing a top sheet layer in a machine direction, the top sheet layer having a first and a second cross-machine direction edge;
   folding over a portion of said top sheet layer at said first and second cross-machine direction edges;
   coupling a pre-folded first side panel to the folded over portion of said first cross-machine direction edge of said top sheet layer at a first edge of said first side panel at a first bond site, wherein said first side panel comprises at least one fold positioned between said folded over portions of said first and second cross-machine direction edges during said coupling; and
   coupling a pre-folded second side panel to the folded over portion of said second cross-machine direction edge of said top sheet layer at a first edge of said second side panel at a second bond site, wherein said second side panel comprises a fold nested within the at least one fold of the pre-folded first side panel.

2. The method of claim 1, said method further comprising providing a back sheet about said coupled portion of said first side panel and said top sheet layer, underneath said top sheet layer, and about said coupled portion of said second side panel and said top sheet layer, and coupling said back sheet to said first side panel and said second side panel.

3. The method of claim 1, further comprising bonding said first side panel to said second side panel at a third bond site wherein said third bond site is located between said first bond site and said second bond site.

4. The method of claim 3, said bonding of said first and second side panels comprising a temporary bond.

5. The method of claim 1 further comprising:
   unfolding the folded portion of the top sheet layer at the first cross-machine direction edge; and
   unfolding the folded portion of the top sheet layer at the second cross-machine direction edge.

6. A method of forming bonds between discrete components of disposable articles, the method comprising:
   providing a top sheet layer in a machine direction, the top sheet layer having a first and a second cross-machine direction edge;
   folding over a portion of the top sheet layer at the first and second cross-machine direction edges;
   coupling a pre-folded first side panel to the folded over portion of the first cross-machine direction edge of the top sheet layer at a first edge of the first side panel at a first bond site, wherein the first side panel comprises at least one fold positioned between the folded over portions of the first and second cross-machine direction edges during the coupling; and
   coupling a pre-folded second side panel to the folded over portion of the second cross-machine direction edge of the top sheet layer at a first edge of the second side panel at a second bond site; and
   nesting a fold of the pre-folded second side panel within the at least one fold of the pre-folded first side panel.

7. The method of claim 6 further comprising:
   folding over a portion of the first side panel, the folded over portion comprising the at least one fold of the first side panel; and
   folding over a portion of the second side panel, the folded over portion comprising the fold of the second side panel.

8. The method of claim 6 further comprising:
   providing a back sheet about the coupled portion of the first side panel and the top sheet layer, underneath the top sheet layer and about the coupled portion of the second side panel and the top sheet layer; and
   coupling the back sheet to the first side panel and the second side panel.

9. The method of claim 6 further comprising bonding the first side panel to the second side panel at a third bond site wherein the third bond site is located between the first bond site and the second bond site.

10. The method of claim 9, wherein bonding the first and second side panels comprises bonding the first and second side panels with a temporary bond.

11. The method of claim 9, wherein bonding the first and second side panels comprises bonding the first and second side panels with a temporary bond.

12. The method of claim 6 further comprising:
unfolding the folded portion of the top sheet layer at the first cross-machine direction edge; and
unfolding the folded portion of the top sheet layer at the second cross-machine direction edge.

13. A method of forming bonds between discrete components of disposable articles, the method comprising:
providing a top sheet layer in a machine direction, the top sheet layer having a first and a second cross-machine direction edge;
folding over the first cross-machine direction edge;
folding over the second cross-machine direction edge;
pre-folding a first side panel;
coupling the pre-folded first side panel to the folded over portion of the first cross-machine direction edge at a first edge of the first side panel at a first bond site, wherein the first side panel comprises at least one fold positioned between the folded over portions of the first and second cross-machine direction edges during the coupling;
coupling a pre-folded second side panel to the folded over portion of the second cross-machine direction edge at a first edge of the second side panel at a second bond site, wherein the second side panel comprises a fold; and
nesting the fold of the second side panel within the at least one fold of the first side panel.

14. The method of claim 13 further comprising:
folding over a portion of the first side panel, the folded over portion comprising the at least one fold of the first side panel; and
folding over a portion of the second side panel, the folded over portion comprising the fold of the second side panel.

15. The method of claim 13 further comprising:
providing a back sheet about the coupled portion of the first side panel and the top sheet layer, underneath the top sheet layer and about the coupled portion of the second side panel and the top sheet layer; and
coupling the back sheet to the first side panel and the second side panel.

16. The method of claim 13 further comprising bonding the first side panel to the second side panel at a third bond site wherein the third bond site is located between the first bond site and the second bond site.

17. The method of claim 13 further comprising:
unfolding the folded-over first cross-machine direction edge; and
unfolding the folded-over second cross-machine direction edge.

* * * * *